United States Patent [19]

Widran et al.

[11] 4,423,727
[45] Jan. 3, 1984

[54] CONTINUOUS FLOW UROLOGICAL ENDOSCOPIC APPARATUS AND METHOD OF USING SAME

[76] Inventors: Jerrold Widran, 60 Estate Dr., Glencoe, Ill. 60022; Helmut Krebs, 4849 N. Kenneth, Chicago, Ill. 60630

[21] Appl. No.: 252,941

[22] Filed: Apr. 10, 1981

[51] Int. Cl.³ .............................................. A61B 17/36
[52] U.S. Cl. ................................. 128/303.15; 128/7; 128/748
[58] Field of Search ....................................... 128/4–8, 128/303.15, 303.14, 303.17, 276, 305, 673, 748

[56] References Cited

U.S. PATENT DOCUMENTS

| | | | |
|---|---|---|---|
| 2,038,393 | 4/1936 | Wappler | 128/7 |
| 3,139,747 | 7/1964 | Ferrell | 73/38 |
| 3,614,954 | 10/1971 | Mirowski et al. | 128/419 D |
| 3,812,855 | 5/1974 | Banko | 128/276 |
| 3,835,842 | 9/1974 | Inglesias | 128/7 |
| 3,850,162 | 11/1974 | Inglesias | 128/6 |
| 3,850,175 | 11/1974 | Inglesias | 128/303.15 |
| 3,900,022 | 8/1975 | Widran | 128/303.15 |
| 3,918,439 | 11/1975 | Zimmer | 128/7 |
| 3,939,839 | 2/1976 | Curtiss | 128/303.15 |
| 4,274,423 | 6/1981 | Mizuno et al. | 128/675 |

Primary Examiner—Michael H. Thaler
Attorney, Agent, or Firm—Bernard L. Kleinke

[57] ABSTRACT

A continuous flow urological endoscopic apparatus includes an endoscope having a reciprocatively-mounted treating device mounted within a sheath thereof. Pump devices establish continuous flow of fluid into and out of the interior of the body cavity to be treated via delivery and return conduits, respectively. According to one aspect of the invention, the return conduit inlet is positioned near the outermost protracted position of the treating device so that the flow of fluid is away from the objective lens of a telescope mounted within the endoscope, thereby enhancing visibility greatly. According to another aspect of the invention, a pressure sensing device is mounted within the sheath for detecting fluid pressure within the body cavity, and an electric conductor conveys signals indicative of such internal pressure within the body cavity, for safety purposes. A control circuit responds to the signals for de-activating the pump device when the fluid pressure within the body cavity exceeds a predetermined unsafe value of pressure.

11 Claims, 6 Drawing Figures

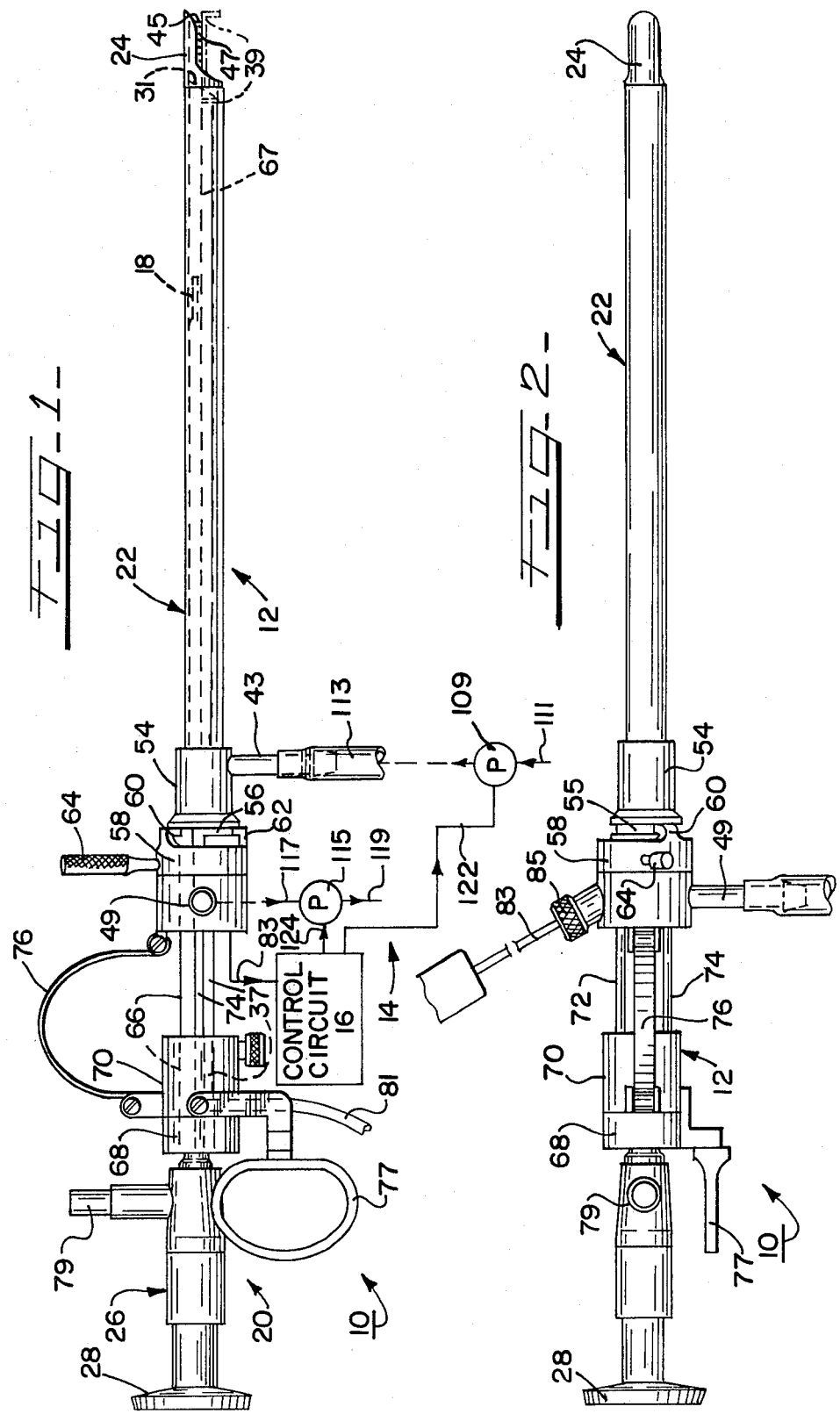

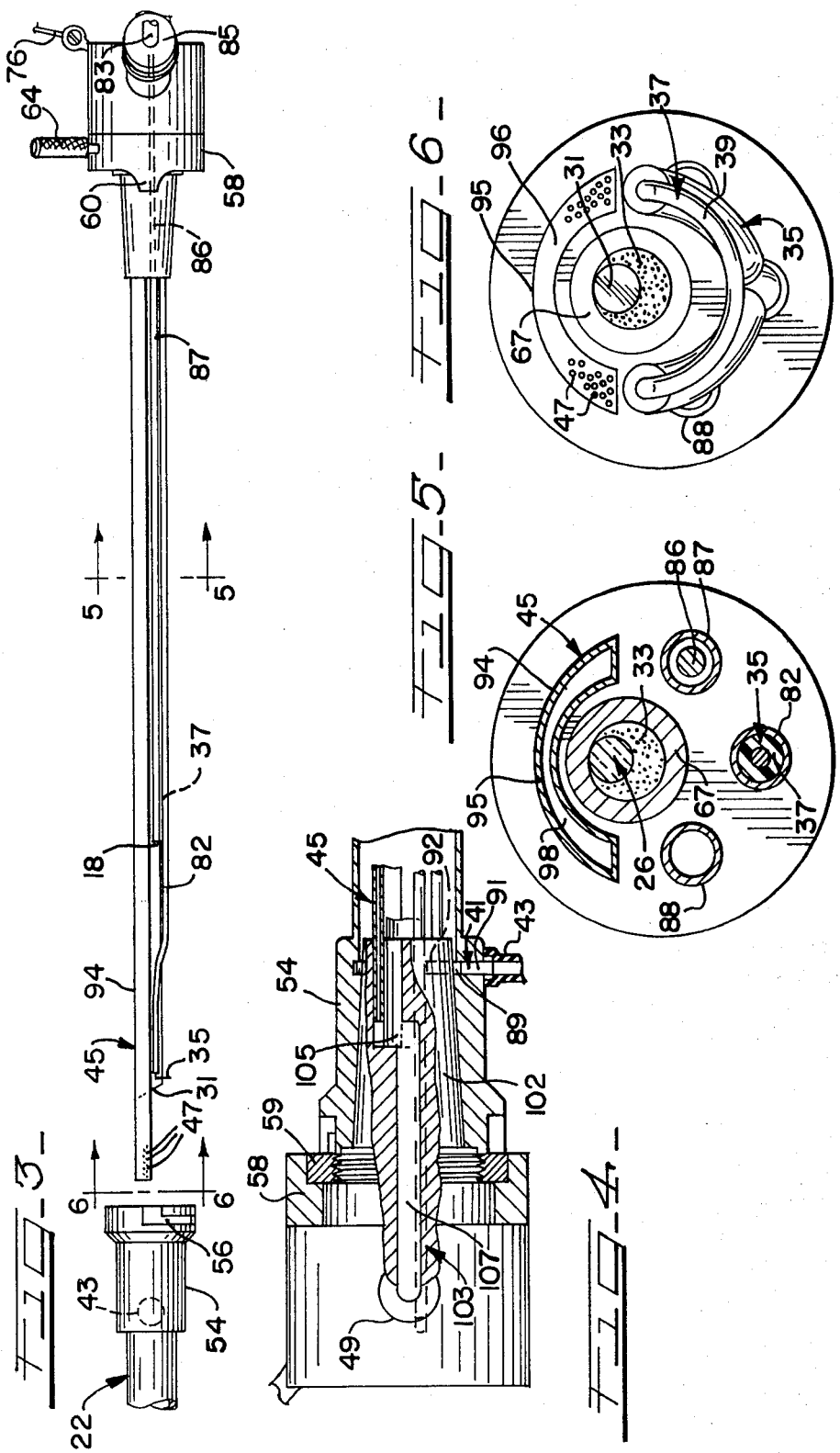

CONTINUOUS FLOW UROLOGICAL ENDOSCOPIC APPARATUS AND METHOD OF USING SAME

DESCRIPTION

TECHNICAL FIELD

The present invention relates in general to a continuous flow urological endoscopic apparatus, and it more particularly relates to endoscopic apparatus, which includes continuous, uninterrupted tissue-irrigating fluid flow pumping equipment.

BACKGROUND ART

There have been many different types and kinds of endoscopes for the examination and treatment of internal body organs. For example, a resectoscope is an endoscope used for transurethral resection of pathological tissues from the prostate or bladder, without the necessity of making an incision. For example, reference may be made to U.S. Pat. No. 3,835,842, which discloses a resectoscope which includes a telescope for viewing the interior of the urethra and the bladder, and an electrically-energizable reciprocatively-movable cutting electrode assembly for resecting pathological body tissues. A clear fluid, such as a water solution, is continuously introduced into the bladder for irrigation purposes to remove blood produced by the resected tissues, by withdrawing turbid fluid continuously from the bladder. In this regard, clear fluid flows under the force of gravity through the resectoscope into the interior of the bladder and from there is pumped from the interior of the bladder back through a return donduit within the resectoscope and into a drain line. In this manner, the operative field is attempted to be continuously irrigated to facilitate proper visualization thereof through the telescope, by attempting to withdraw the bloody turbid fluid continuously from the interior of the bladder.

However, should the volumetric flow rate of turbid fluid flowing from the interior of the bladder decrease relative to the clear fluid entering the interior of the bladder, intra-vesical pressure increases. Such a pressure increase is highly undesirable and can be highly dangerous, if not fatal, to the patient. Increase in intra-vesical pressure can cause an increased rate of absorption of fluid by the prostatic fossa, thereby resulting in chronic distention post-operatively. Also, sufficient increase in intra-vesical pressure can even cause the bladder to rupture. No provision is made for preventing such unsafe increases in intra-vesical pressure in the foregoing-mentioned patented instrument.

Additionally, in U.S. Pat. No. 3,835,842, the inlet to the return conduit for the resectoscope, is disposed on the outside of the unit and can, under certain circumstances, draw adjacent body tissue into blocking and even sealing engagement therewith, thereby increasing the intra-vesical pressure. Such a pressure increase is not only unsafe to the patient, but also a build up of turbid fluid results and thereby greatly obstructs the view of the physician. As a result, the operation must be interrupted frequently, and each time the bladder must be drained and the procedure repeated.

Moreover, turbid fluid flows into the return inlet and at least partially in front of the objective lens, thereby at least partially obstructing the view therefrom. Also, when the cutting electrode is fully protracted out of and away from the sheath of the endoscope to perform a surgical procedure, the greater distance away from the return outlets causes a corresponding decrease in negative pressure differential, whereby more of the bloody fluid remains in the body cavity.

In order to monitor the intra-vesical pressure, endoscopes have been provided with pressure-monitoring equipment to synchronize the volumetric flow rates, into and out of the bladder. In this regard, reference may be made to U.S. Pat. No. 3,900,022, which discloses both a delivery pump and a suction pump for fluid circulation at relatively high flow rates. Also, included are pressure gauges and other devices for monitoring the flow of fluid into and out of the endoscope. However, while such an endoscope and irrigation system are satisfactory for some applications, it would be highly desirable to have such a high volumetric flow rate together with highly accurate safety devices to prevent, or to at least greatly minimize, unsafe increases in intra-vesical pressure.

Therefore, it would be highly desirable to have a new and improved endoscope which provides for a much greater flow rate of fluid, substantially without vision-obstruction turbulence, so as to more greatly enhance the visibility of the operative field for much longer periods of time. Also, such a new and improved endoscope should have safety devices for preventing, or at least greatly minimizing unsafe build up of intra-vesical pressure.

DISCLOSURE OF INVENTION

Therefore, the principal object of the present invention is to provide a new and improved continuous flow urological endoscopic apparatus, which circulates irrigation fluid at relatively high flow rates, and which efficiently and effectively prevents, at least greatly minimizes, unwanted and undesirable increases in pressure within the interior of the body cavity during a procedure.

Another object of the present invention is to provide such a new and improved continuous flow urological endoscopic apparatus, which also enhances greatly the view of the operative field for longer periods of time.

Briefly, the above and further objects of the present invention are realized by providing a continuous flow urological endoscopic apparatus, which includes a endoscope having a reciprocatively-mounted treating device, such as a cutting electrode assembly, at least partially within the sheath of the endoscope. For circulating irrigation fluid into and out of a body cavity for flushing purposes, a delivery conduit is adapted to be connected in fluid communication with a source of clear irrigating fluid under pressure for conveying clear irrigating fluid under pressure to the interior of the body cavity via the open end of the sheath. A return conduit is adapted to be connected in fluid communication with a drain line for withdrawing turbid fluid from the interior of the body cavity. A return conduit inlet is connected in fluid communication with the return conduit and is positioned within the sheath forwardly by a substantial axial distance from the objective lens of a telescope, and spaced radially from the axis of the lens. The return conduit inlet directs turbid fluid forwardly away from the objective lens for clearing turbid fluid continuously away from the field of view of the objective lens, thereby enhancing greatly the visibility of the operative field for much longer periods of time. The return inlet is positioned near the outermost protracted position of the cutting electrode of the electrode assembly so that the flow of fluid is away from the objective lens and also provides for good negative pressure for the return flow of fluid with the electrode fully protracted. Also, the return inlet is protected by the beak of the sheath and is normally disposed within the body cavity away from body tissue which could otherwise be drawn into blocking engagement with the return inlet.

A pressure sensing device is mounted within the sheath for detecting fluid pressure within the body cavity, and an electric conductor is connected to the sensing device for conveying signals indicative of the internal pressure within the body cavity for safety purposes. Pump devices establish the continuous flow of fluid into and out of the interior of the body cavity via the delivery and return conduits, respectively. A control circuit responds to the signals from the pressure sensing device via the electric conductor for de-activating the pump device quickly and safely, when the fluid pressure within the body cavity exceeds a predetermined unsafe value of pressure, thereby stopping the flow of irrigation fluid.

BRIEF DESCRIPTION OF DRAWINGS

The above-mentioned and other objects and features of this invention and the manner of attaining them will become apparent, and the invention itself will be best understood by reference to the following description of an embodiment of the invention taken in conjunction with the accompanying drawings, wherein:

FIG. 1 is a right side elevational and partly schematic view of the continuous flow urological endoscopic apparatus, which is constructed in accordance with the present invention;

FIG. 2 is a plan view thereof;

FIG. 3 is a fragmentary, enlarged left side elevational view, showing the endoscope partially disassembled;

FIG. 4 is a right side sectional elevational view, with portions thereof broken away for illustration purposes, of an intermediate portion of the endoscope of FIG. 1, shown at a greatly enlarged scale;

FIG. 5 is a greatly enlarged sectional view of the endoscope of FIG. 3, taken substantially along the line 5—5 thereof; and FIG. 6 is a front end view of the endoscope of FIG. 3, taken substantially along the line 6—6 thereof.

BEST MODE FOR CARRYING OUT THE INVENTION

Referring now to the drawings, and more particularly to FIGS. 1 and 2 thereof, there is shown a urological endoscopic apparatus 10, which is constructed in accordance with the present invention. The apparatus 10 generally comprises an endoscope 12 for entering a human body cavity (not shown), such as the urethra and the bladder, for visual inspection and treatment thereof, and fluid pumping equipment generally indicated at 14 for circulating suitable irrigation fluid into and out of the interior of the body cavity for removal of blood produced by the resected tissue from the operative field, to maintain a clear view thereof. While the endoscope, shown and described herein, is a resectoscope, it will become apparent to those skilled in the art, that the principles of the present invention are also applicable to other types of endoscopes as well.

For safety purposes, a control circuit 16 de-energizes the fluid pumping equipment 14 once the pressure within the body cavity, such as a bladder, exceeds a certain unsafe predetermined value of pressure. As shown in FIGS. 1 and 3 of the drawings, a highly sensitive pressure sensor 18 is mounted within the body cavity, and thus for generating an electrical signal for supplying it to the control circuit 16, thereby enabling the internal pressure of the body cavity to be monitored and the recirculating fluid can be stopped once the predetermined value of pressure is exceeded in accordance with the present invention.

The endoscope 12 includes a hand-held rear end portion 20, which is adapted to be grasped by the fingers of the physician during the operative procedure. An elongated tubular sheath 22 extends forwardly from the hand-held portion 20 and terminates at its forward distal end in a beak 24, which has an open front end to facilitate insertion into the interior of the body cavity.

As best seen in FIGS. 1, 5 and 6 of the drawings, a conventional elongated telescope 26 extends within the sheath 22 between an eye piece 28, at the rear end thereof, and an objective lens 31 at the front end thereof. An ocular lens (not shown) is mounted within the telescope 26. As best seen in FIGS. 5 and 6 of the drawings, a fiber optic light conductor 33 extends through the telescope 26 and is adapted to emit light from the front end thereof at the objective lens 31. As best seen in FIG. 6 of the drawings, a reciprocatively mounted treating device 35 including an elongated cutting electrode assembly 37 disposed within the sheath 22. A cutting wire loop 39 depends from the front end of the electrode assembly, and is adapted to resect tissue. The electrode assembly is conventional, and a suitable one is manufactured by the Carl Stortz Company and distributed by the Mueller Corporation of Chicago, Illinois.

As best seen in FIG. 4 of the drawings, a delivery conduit 41 conveys irrigating fluid under pressure, from an exterior delivery inlet 43 adapted to receive fluid under pressure, to the interior of the sheath. Thus, fluid flows from the beak 24 and into the interior of the body cavity.

A return conduit 45 extends within the interior of the sheath 22 and has a return inlet 47 disposed within the forward end of the elongated beak 24 spaced axially by a substantial distance in front of the objective lens 31, and an exterior return outlet 49 adapted to convey turbid fluid therefrom. It should be noted that the return outlet 49 is positioned slightly within the outermost tip portion of the beak 24, and to the rear of the outermost protracted position of the wire loop 39, as indicated in phantom lines in FIG. 1.

In operation, clear fluid flows forwardly from the sheath and into the body cavity, and is continuously drawn into the return inlet 47. As a result, turbid fluid is drawn continuously forwardly and upwardly away from the field view of the objective lens 31. When the electrode assembly is energized to resect bodily tissue, the wire loop 39 is advanced from its fully retracted position, shown in broken lines in FIG. 1, out of the end of the beak 24 to a desired position for performing the surgery. Resulting blood is swept upwardly and away from the objective lens, and into the return inlet. The return flow continues, even when the wire loop 39 is disposed at its outermost protracted position, beyond the tip end of the beak 24, as indicated in phantom lines in FIG. 1. Even in the fully protracted position, blood flowing from resected tissue is swept into the return inlet 47, which is closely spaced relative to the protracted wire loop 39.

Considering now the hand-held portion 20 in greater detail, a cylindrical socket base block 52 is releasably and sealably connected to an enlarged rear end portion 54 of the sheath 22 so that the unit can be readily disassembled. A pair of external peripheral bayonet slots 55 and 56 in the enlarged end portion 54 receive a pair of diametrically opposed locking fingers 60 and 62 projecting forwardly from a rotatable locking ring or collar 58, held in place rotatably by a nut or ring 59 on the locking collar 58 at the front end of the base block 52. An external projection or rod 64 is fixed to and extends radially from the locking collar 58 to facilitate the rotation thereof, when the projection 64 is grasped by the fingers of the user, to either lock or unlock the enlarged rear end portion 54 of the sheath to the socket base block 52.

As best seen in FIGS. 5 and 6, a telescope receiving tube 66 surrounds a tubular housing 67 of the telescope 26 and extends between a fixed cylindrical end block 68 through a longitudinally-extending opening (not shown) in a cylindrical slide block 70 and fixed at its forward end to the fixed base block 52. A pair of parallel, spaced-apart guide rods or runners 72 and 74 are fixed in position and extend between the base block 52 and the end block 68 through openings (not shown) in the slide block 70, on opposite sides of the telescope receiving tube 66, to guide the slidable movement of the slide block 70, which moves toward and away from the end block 68. A return spring 76 is fixed between the base block 52 and the slide block 70 to bias it into engagement with the end block 68 as best seen in FIG. 1. A thumb holder 77 at one side of the cylindrical block 70 enables the user to pull the slide block 70 forwardly toward the radial projection 64 on the locking collar 58, thereby to advance the electrode assembly 37 forwardly of the front end of the beak 24 toward a maximum position as indicated in phantom lines in FIG. 1.

A light source connector 79 extends radially outwardly from the telescope near the eye piece 28 and is adapted to be connected to a suitable source (not shown) of light for illuminating the fiber optic light conductor 33 for illuminating the interior of the body cavity.

As best seen in FIG. 1, a power conductor 81 extends radially into the slide block 70 and is connected electrically to the rear end of the electrode assembly 37. As best seen in FIG. 5, an electrode support tube 82 surrounds the electrode assembly 37 to support it directly below the telescope 26.

As best seen in FIGS. 2 and 3, an external conductor 83 is attached to the endoscope 12 by means of an electrical connector 85 to an internal sensor conductor 86 disposed within a protective support tube 87 (FIG. 5) extending on the left side of the endoscope 12 within the sheath 22. The pressure sensor 18 is connected electrically to the forwardmost end of the conductor 86 and is positioned as far forwardly as possible within the sheath. In this manner, the sensor 18 responds to the pressure within the body cavity, and not merely to the pressure of the clear fluid flowing through the interior of the sheath. The sensor is highly sensitive, and should be of the type that is accurate, approximately, to within 1/10 of a centimeter of pressure.

The pressure sensor 18 is a transducer, and a suitable one is known by the registered trademark, "Millar Mikro-tip", for a catheter pressure transducer, which may be obtained from Millar Instruments, Inc., P.O. Box 18227, 6001 Gulf Freeway, Houston, Texas 77023.

A hollow support rod 88 extends on the right side of the endoscope, in a spaced-apart manner opposite the tube; 87 to help rigidify the unit throughout its length.

Considering now the delivery conduit 89 in greater detail with particular reference to FIG. 4 of the drawings, the delivery conduit generally indicated at 41 includes a radially extending passageway 91 within the enlarged rear end portion 54 of the sheath 22 and connects the delivery inlet 43 in fluid communication with an internal annular passageway 89, also forming a portion of the conduit 41, to deliver fluid under pressure through a series of internal peripheral slit openings, such as the opening 92, which open into the interior of the sheath 22. Thus, the delivery conduit 41 extends in fluid communication between the delivery inlet 43, the passageway 91, the passageway 89, through the slit openings and into and including the interior of the sheath 22 for guiding the fluid under pressure through the sheath and out the open end of the beak 24.

Considering now the return conduit 45 in greater detail, the return conduit 45 includes a return tube 94 extending within the sheath 22, for substantially the length thereof, and disposed at the upper internal portion thereof. The return tube 94 is generally C-shaped or crescent-shaped in cross-section throughout its length, and has a central restricted or narrowed area 95 at the upper portion thereof. The tube 94 is disposed with its concave contour facing downwardly and is spaced from and nested above the telescope tube 67. The return inlet 47 comprising a series of holes in the front end portion of the tube 94. The holes are smaller in diameter than the restricted area 95 to insure that blood clots or the like entering the holes 47 are sufficiently small in size to pass freely through the restricted area 95 without clogging it.

As best seen in FIG. 6 of the drawings, the tube 94 has a front wall 96 having some of the holes 47 in the sides of the front end of the tube 94, and some of the holes 47 at opposite sides thereof, but not in the central restricted or narrow area 95 disposed directly above the object lens 31, so as to avoid drawing turbid fluid in direct line therewith. The tube 94 terminates rearwardly at an open rear end portion 98 seated within a complementary-shaped open slot 101 in a reduced diameter, tapered portion 101 of the base block 52, as best seen in FIG. 4 of the drawings. A passageway 103 in the tapered portion 102 connects the tube 45 in fluid communication with the return outlet 49, and includes a radially-extending portion 105 connected in fluid communication between the complementary-shaped open slot 101 and a rearwardly-extending axial portion 107, which, in turn, is connected in fluid communication with the return outlet 49.

In this manner, the tube 94 is able to convey a relatively large quantity of fluid rearwardly therethrough to provide for excellent circulation of fluid at high flow rates, without undue turbulence. The tube 94 is preferably insulated electrically by providing it with a suitable external coating (not shown) of plastic material so that the high frequency electrical energy supplied to the electrode assembly 37 does not discharge to the tube 94.

Considering now the fluid pumping equipment 14 in greater detail with reference to FIG. 1, the equipment 14 includes an inlet pump 109 for discharging fluid under pressure from a fluid line 111 connected in fluid communication to a source (not shown) of fluid under pressure. A discharge conduit or tube 113 connects the discharge outlet of the pump 109 in fluid communication with the inlet 43 of the delivery conduit 41. Thus, fluid under pressure is pumped from the fluid line 111 through the inlet 43 and the delivery conduit 41 to the interior of the body cavity, such as a human bladder.

The pumping equipment 14 further includes a suction pump 115 having its inlet connected via a suction line 117 in fluid communication with the return outlet 49. A drain line 115 is connected to the discharge outlet of the pump 115.

The conductor 83 of the sensor 18 is connected to a control circuit 16 which monitors the pressure within the interior of the body cavity. When the pressure reaches the predetermined unsafe value, the control circuit 16 supplies electrical signals, indicative of the unsafe condition, via a pair of electrical conductor leads 122 and 124 to the pumps 109 and 115, respectively, for de-energizing them. The control circuit 16 is preferably a DC ammeter having suitable set points (not shown) for generating the signals for the leads 122 and 124 at preselected values of pressure.

While a particular embodiment of the present invention has been disclosed, it is to be understood that various different modifications are possible and are contemplated within the true spirit and scope of the appended claims. For example, different materials may be employed for different parts of the endoscope. There is no intention, therefore, of limitations to the exact abstract or disclosure herein presented.

We claim:

1. Continuous flow urological endoscopic apparatus for insertion into a body cavity, comprising: an endoscope including an outer tubular sheath having a forwardly-disposed beak, said beak having an open front end; an elongated telescope being disposed at least partially within the interior of said sheath and having a fowardly mounted objective lens for viewing the interior of the body cavity; means for positioning said objective lens spaced axially by a substantial distance rearwardly from said open front end; light conductor means mounted within said sheath for permitting the interior of the body cavity to be illuminated; treating means reciprocatively mounted at least partially within the front end portion of said sheath for moving forwardly and rearwardly; pumping means for impelling fluid into and for causing discharge from a treatment zone within the body cavity; delivery conduit means adapted to be connected to fluid communication with said pumping means for conveying fluid to the interior of the body cavity via said open-ended beak; return conduit means adapted to be connected in fluid communication with said pumping means for withdrawing turbid fluid from the interior of the body cavity; return conduit inlet means connected in fluid communication with said return conduit, and positioned forwardly by a substantial axial distance from said objective lens and spaced radially from the axis of said lens for directing turbid fluid to said return conduit to clear turbid fluid away from the field of view of said objective lens; a single pressure sensing means disposed within said sheath for detecting fluid pressure directly and continuously within the body cavity; electric conductor means connected electrically to said sensor means and extending therefrom within said sheath and outwardly therefrom to send signals indicative of the internal pressure within the body cavity; control means responsive to said signals indicative of said sensor means detecting predetermined, selectable threshold pressures developed in the body cavity for de-activating promptly said pumping means thereby obviating development of physiologically objectionable fluid pressure in the body cavity during use of said endoscope; said return conduit means including a return tube, said tube being positioned within said sheath and extending along the upper interior portion thereof, said return tube being substantially C-shaped throughout its length and being positioned concave downwardly above the upper portion of the telescope, said tube having a central restricted area at the upper portion thereof, said telescope being disposed adjacent to said restricted portion of said return tube, said treating means, said electric conductor means and said sensing means being disposed below said telescope.

2. Continuous flow urological endoscopic apparatus according to claim 1, further including electric conductor means connected electrically to said sensing means and adapted to send signals indicative of the internal pressure within the body cavity.

3. A continuous flow urological endoscopic apparatus according to claim 2, further including pump means for establishing a continuous flow of fluid into the interior of the body cavity via said delivery conduit means and out said return conduit means, control circuit means responsive to said signals for de-activating said pump means when the fluid pressure within the body cavity exceeds a predetermined value of pressure.

4. A continuous flow urological endoscopic apparatus according to claim 1, wherein said central restricted area of said tube is a narrowed imperforate central portion, said return conduit inlet means including means defining holes in the front end portion of said return tube.

5. A continuous flow urological endoscopic apparatus according to claim 4, wherein said endoscope further includes a rear end portion having a manually slidably movable block mounted between an end block and a base block, said treating means being a cutting electrode assembly extending fowardly from said movable block through an opening in said base block and into said sheath, spring means for biasing said movable block into engagement with said end block.

6. Continuous flow urological endoscope apparatus for insertion into a body cavity, comprising; an endoscope including an outer tubular sheath having a forwardly-disposed beak, said beak having an open front end; an elongated telescope being disposed at least partially within the interior of said sheath and having a forwardly mounted objective lens for viewing the interior of the body cavity; light conductor means mounted within said sheath for permitting the interior of the body cavity to be illuminated; treating means mounted at least partially within the front end portion of said sheath; delivery conduit means adapted to be connected in fluid communication with a source of clear irrigating fluid to the interior of the body cavity via the open-ended beak; return conduit means adapted to be connected in fluid communication with a drain line for withdrawing turbid fluid from the interior of the body cavity; a single pressure sensing means mounted forwardly within said sheath behind said treating means for detecting fluid pressure directly and continuously within the body cavity; electric conductor means connected electrically to said sensing means and extending therefrom within said sheath and outwardly therefrom to send signals indicative of the internal pressure within the body cavity; pump means for establishing a continuous flow of fluid into the interior of the body cavity via said delivery means and out said conduit means; control circuit means responsive to said signals indicative of said sensor means detecting predetermined, selectable threshold pressures developed in the body cavity for de-activating promptly said pumping means thereby obviating development of physiologically objectionable fluid pressure in the body cavity during use of said endoscope.

7. A continuous flow urological endoscopic apparatus according to claim 6, wherein said return conduit means includes a return tube, said tube being positioned within said sheath and extending along the upper interior portion thereof.

8. A continuous flow urological endoscopic apparatus according to claim 7, wherein said return tube being C-shaped throughout its length and being positioned concave downwardly above the front portion of the telescope, said tube having a central restricted area at the upper portion thereof, said telescope being disposed adjacent to said restricted portion of said return tube, said treating means and said sensing means being disposed below said telescope.

9. A continuous flow urological endoscopic apparatus according to claim 6, wherein said control means includes a set-point ammeter for generating said signal.

10. In an endoscope for use in medical examination and surgical treatment within a body cavity and including:
   an elongated tubular sheath for insertion longitudinally through a restricted body passage communicating with a body cavity,
   first conduit means within said sheath for transmittal of a fluid stream through said sheath and through said restricted passage into a treatment zone in which a surgical technique is to be conducted within the body cavity,
   second conduit means within said sheath for removal of fluid from said treatment zone through said restricted passage,
   pumping means for impelling fluid into and for causing discharge from said treatment zone of the body cavity,
   optical means including lens means for viewing said treatment zone,
   lighting means for illuminating said treatment zone,
   means for treating tissue at said treatment zone,
   the improvement comprising:
   sensor means disposed forwardly within said sheath of said endoscopic apparatus behind said tissue treatment means and in functional communication with said treatment zone for monitoring fluid pressure directly and continuously in the body cavity;
   electric conductor means connected electrically to said sensor means and extending therefrom within said sheath and outwardly therefrom to send signals indicative of the internal pressure within the body cavity; and
   control means responsive to said signal indicative of said sensor means detecting predetermined, selectable threshold pressure developed in the body cavity for de-activating promptly said pumping means thereby obviating development of physiologically objectionable fluid pressures in the body cavity during use of said endoscope.

11. A method of using an endoscope including an enveloping tubular sheath, fluid conduit means including fluid inlet means, and fluid exhaust means disposed within said sheath, said conduit means extending longitudinally through said sheath for presentation into a restricted passage communicating with a body cavity for transmittal of a fluid stream through said passage and into and from a treatment zone subjected to a surgical procedure, tissue treatment means including means for removing tissue from said treatment zone, optical means including lens means at a distal end of said optical means for viewing said treatment zone,
   the improvement comprising the steps of flowing fluid into said fluid inlet means and out said fluid exhaust means; detecting body cavity fluid pressure directly and continuously, at a forward interior portion of said sheath, during flow of fluid into and out of the body cavity; continuously generating electrical signals indicative of said body cavity fluid pressure and conveying them outside of said sheath; and interrupting said fluid flow in response to said signals indicating an undesirable body cavity pressure.

* * * * *

UNITED STATES PATENT AND TRADEMARK OFFICE
CERTIFICATE OF CORRECTION

PATENT NO. : 4,423,727
DATED : January 3, 1984
INVENTOR(S) : Jerrold Widran, Helmut Krebs It is certified that error appears in the above—identified patent and that said Letters Patent is hereby corrected as shown below:

Column 7, line 47, after the word "connected", delete "to" and substitute --in-- therefor.

Signed and Sealed this

Seventeenth Day of April 1984

[SEAL]

Attest:

GERALD J. MOSSINGHOFF

Attesting Officer

Commissioner of Patents and Trademarks